(12) United States Patent
Nonaka et al.

(10) Patent No.: US 6,523,419 B1
(45) Date of Patent: Feb. 25, 2003

(54) ELECTRODE TENSILE TEST METHOD AND APPARATUS, SUBSTRATE/PROBE SUPPORT DEVICE FOR ELECTRODE TENSILE TEST, AND ELECTRODE-PROBE BONDING DEVICE FOR ELECTRODE TENSILE TEST

(75) Inventors: Nobuyoshi Nonaka, Chiba (JP); Tadashi Torimitsu, Chiba (JP)

(73) Assignee: Kabushiki Kaisha Arctek, Chiba-ken (JP)

( * ) Notice: Subject to any disclaimer, the term of this patent is extended or adjusted under 35 U.S.C. 154(b) by 0 days.

(21) Appl. No.: 09/535,612

(22) Filed: Mar. 27, 2000

(30) Foreign Application Priority Data

Apr. 2, 1999 (JP) .............................. 11-096980
Feb. 28, 2000 (JP) ........................ 2000-052340

(51) Int. Cl.[7] .................................. G01N 3/08
(52) U.S. Cl. ............................... 73/827; 73/831
(58) Field of Search ................. 73/826, 827, 835, 73/834, 831

(56) References Cited

U.S. PATENT DOCUMENTS 5,641,913 A * 6/1997 Watanabe ................. 73/827
5,969,262 A * 10/1999 Ino et al. .................. 73/827

FOREIGN PATENT DOCUMENTS

| JP | 57-2550 |   | 1/1982 |
| JP | 1215046 | * | 2/1988 |
| JP | 3-156950 |   | 7/1991 |
| JP | 08111417 |   | 4/1996 |
| JP | 410150078 | * | 11/1997 |
| JP | 000091465 | * | 9/1998 |
| JP | 11-297763 |   | 10/1999 |

* cited by examiner

Primary Examiner—Benjamin R. Fuller
Assistant Examiner—Lilybett Martir
(74) Attorney, Agent, or Firm—Merchant & Gould P.C.

(57) ABSTRACT

An electrode tensile test method and apparatus which can yield accurate data, and a substrate/probe support device for an electrode tensile test. For this purpose, the electrode tensile test method includes a heating step (S202) of heating the ambient temperature of a space containing the probe and the electrode, an inserting step of inserting the probe into the electrode fused by the heating step, a cooling step (S203) of cooling the electrode, in which the probe has been inserted by the inserting step, together with the probe, and the measuring step (S205, S206) of pulling the probe, fixed to the electrode through the cooling step, from the substrate, and measuring the tensile strength.

17 Claims, 14 Drawing Sheets

FIG. 10A        FIG. 10B        FIG. 10C
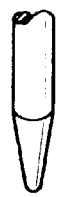  
FIG. 10D        FIG. 10E
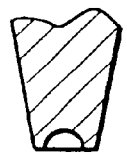 
FIG. 10F        FIG. 10G        FIG. 10H
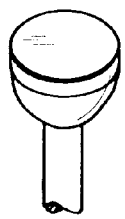 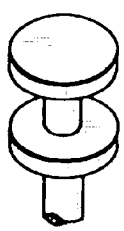 
FIG. 10I   FIG. 10J   FIG. 10K   FIG. 10L
   
FIG. 10M
FIG. 10N        FIG. 10O
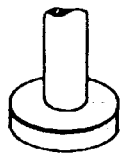 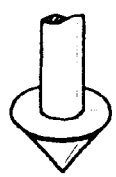

F I G. 14
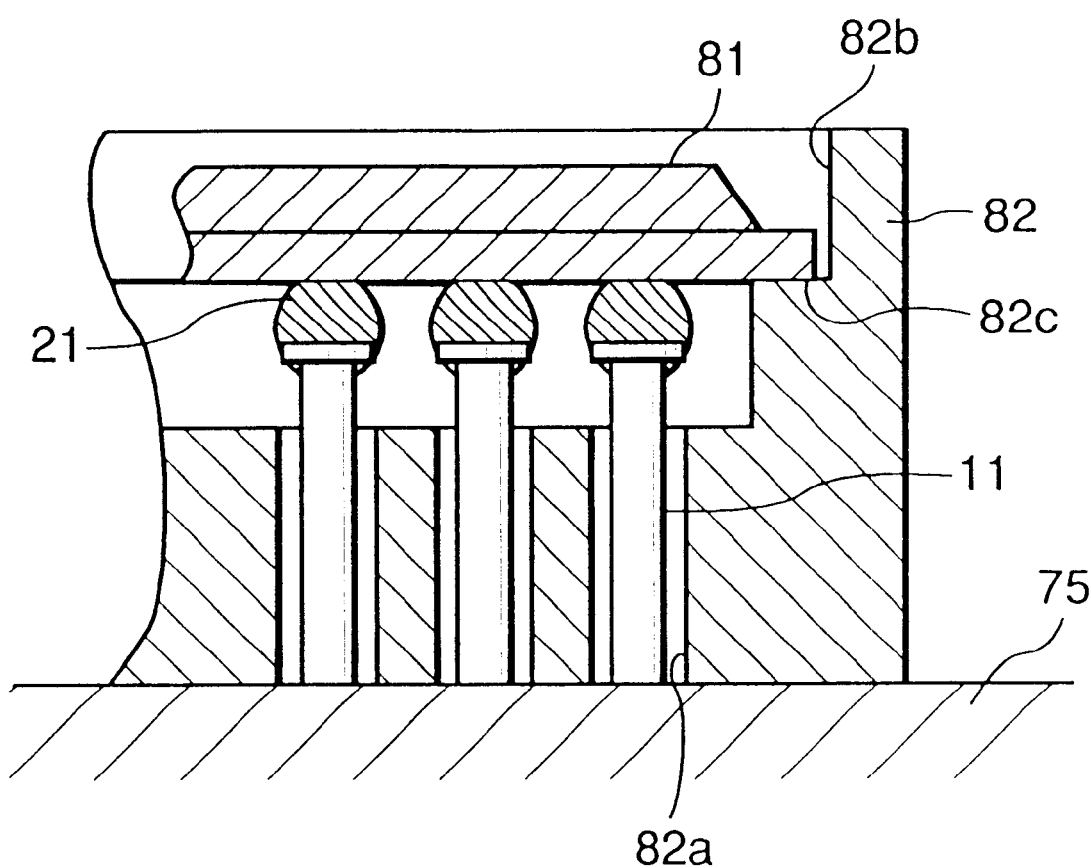

ELECTRODE TENSILE TEST METHOD AND APPARATUS, SUBSTRATE/PROBE SUPPORT DEVICE FOR ELECTRODE TENSILE TEST, AND ELECTRODE-PROBE BONDING DEVICE FOR ELECTRODE TENSILE TEST

FIELD OF THE INVENTION

The present invention relates to an electrode tensile test method and apparatus for testing the tensile strength between a substrate and an electrode by using a probe, a substrate/probe support device for an electrode tensile test, and an electrode-probe bonding device for an electrode tensile test.

BACKGROUND OF THE INVENTION

Packaging high integration density is recently demanded to reduce the cost of electronic devices in computers, automobiles, home electric appliances, and the like and to downsize them into small, low-profile devices. Among several high-density packaging methods that are currently available, a packaging method using a bump electrode (e.g., BGA, CSP, flip chip, TAB, or the like) attracts attention because it requires a smaller bonding area than other packaging methods while providing a high bonding strength.

The reliability of the packaging method of this type include the tensile strength between a bump electrode and a substrate land. In order to examine this tensile strength, a bump electrode tensile test is generally used.

As an electrode tensile test method of this type, for example, the method disclosed in Japanese Patent Laid-Open No. 8-111417 is known. According to this method, a probe is directly heated by using a heater. A bump electrode is fused with the heat of the probe and is bonded with the probe. Then, the probe is pulled to test the bonding strength between the bump electrode and the substrate.

An actual packaging process, however, does not heat only a member to be connected to the bump electrode. When the above prior art is used, the substrate and the electrode as the members to be tested undergo a temperature condition different from that in the actual packaging process, and the resultant tensile strength is sometimes different from that of an actual product.

In the method disclosed in Japanese Patent Laid-Open No. 8-111417 described above, each time one bump is to be measured, a procedure including heating, fusion, cooling, and measurement must be performed. Hence, measurement takes time.

SUMMARY OF THE INVENTION

The present invention has been made in order to solve the problems of the prior art, and has as its object to provide an electrode tensile test method and apparatus which can provide test results of an electrode tensile strength closer to that obtained in a packaging process, a substrate/probe support device for an electrode tensile test, and an electrode-probe bonding device for an electrode tensile test.

It is another object of the present invention to provide an electrode tensile test method and apparatus, which can run an electrode tensile test efficiently, a substrate/probe support device for an electrode tensile test, and an electrode-probe bonding device for an electrode tensile test.

According to the present invention, the foregoing object is attained by providing an electrode tensile test method of fixing a probe and an electrode on a substrate to each other, and pulling the probe, thereby testing the tensile strength of the electrode with respect to the substrate, comprising: an electrode fusing step of fusing the electrode; an inserting step of inserting the probe into the electrode fused by the electrode fusing step: a cooling step of cooling the electrode, into which the probe has been inserted by the inserting step, together with the probe; and a measuring step of pulling the probe, fixed to the electrode through the cooling step, from the substrate, and measuring the tensile strength between the electrode and the substrate.

In a preferred embodiment, the inserting step is the step of inserting the probe into the fused electrode using the weight of the probe itself.

According to the present invention, the foregoing object is attained by providing an electrode tensile test method of fixing a probe and an electrode on a substrate to each other, and pulling the probe, thereby testing the tensile strength of the electrode with respect to the substrate, comprising: an inserting step of inserting the probe into the electrode; an electrode fusing step of directly applying heat to the electrode into which the probe has been inserted, thereby fusing the electrode; a cooling step of cooling the electrode, fused by the electrode fusing step, together with the probe; and a measuring step of pulling the probe, fixed to the electrode through the cooling step, from the substrate, and measuring the tensile force between the electrode and the substrate.

In a preferred embodiment, the electrode fusing step is the step of increasing an ambient temperature of a space including the probe and the electrode.

In a preferred embodiment, the electrode fusing step comprises heating the substrate and the probe in a reflow furnace.

In a preferred embodiment, the electrode fusing step is the step of placing the substrate and the probe in a chamber, and blowing heated air into the chamber, thereby heating the interior of the chamber.

In a preferred embodiment, the electrode fusing step comprises blowing at least nitrogen into the chamber.

In a preferred embodiment, the electrode fusing step comprises the step of applying heat to the electrode through the substrate.

In a preferred embodiment, the inserting step is the step of arranging the substrate above the probe and inserting the probe facing up into the electrode facing down.

In a preferred embodiment, the inserting step comprises the positioning step of defining a position of the substrate with respect to the probe.

In a preferred embodiment, in each of the electrode fusing step, the inserting step, and the cooling step, a plurality of electrodes on one substrate and a plurality of probes corresponding thereto are processed simultaneously.

Further, according to the present invention, the foregoing object is also attained by providing an electrode tensile test apparatus for fixing a probe to an electrode and pulling the probe, thereby testing the tensile strength of the electrode with respect to a substrate, comprising: electrode fusing means for directly applying heat to the electrode, thereby fusing the electrode; and measuring means for pulling the probe which is inserted in the electrode fused by the heating means and is cooled so as to be fixed to the electrode, from the substrate, and measuring a tensile force between the electrode and the substrate.

In a preferred embodiment, the electrode fusing means is heating means for increasing the ambient temperature of space including the probe and the electrode.

In a preferred embodiment, the heating means is a reflow furnace.

In a preferred embodiment, the heating means comprises: a chamber in which the substrate and the probe are placed; and means for blowing heated air into the chamber, thereby heating the interior of the chamber.

In a preferred embodiment, the heating means has means for blowing at least nitrogen into the chamber.

In a preferred embodiment, the electrode fusing means comprises substrate heating means for heating the substrate in order to transmit heat to the electrode through the substrate.

In a preferred embodiment, the apparatus further having: substrate support means for supporting the substrate; and probe guiding means for guiding the probe to the electrode.

In a preferred embodiment, the probe guiding means guides a plurality of probes to a plurality of electrodes simultaneously.

In a preferred embodiment, the substrate support means supports the substrate to face down; and the probe guiding means supports the probe to face up; wherein the substrate support means and the probe guiding means being arranged such that the substrate is located above the probe.

In a preferred embodiment, the substrate support means has positioning means for defining the distance between the distal end of the probe and the substrate.

In a preferred embodiment, the probe has a rod-like portion, and a distal end portion to be fixed to the electrode, the probe guiding means is a plate-like member having a probe inserting hole with a larger diameter than that of the rod-like portion, the substrate support means has a support for supporting the plate-like member to be substantially parallel to the substrate, and the support serves to support the plate-like member such that, when the probe is inserted in the hole in the plate-like member and the distal end portion thereof abuts against the electrode on the substrate supported by the substrate support means, at least part of the rod-like portion of the probe projects to that side of the plate-like portion which opposes the substrate.

Further, according to the present invention, the foregoing object is also attained by providing an electrode tensile test apparatus for fixing a probe to an electrode and pulling the probe, thereby testing the tensile strength of the electrode with respect to a substrate, comprising heating means having a heater and capable of soldering an electronic component; and measuring means for pulling a plurality of probes, which are inserted in a plurality of electrodes fused by the heating means and cooled so as to be fixed to the electrodes, and measuring a tensile force between the electrode and the substrate.

Further, according to the present invention, the foregoing object is also attained by providing a substrate/probe support device for an electrode tensile test for fixing a probe and an electrode on a substrate to each other by using heating means which increases an ambient temperature, and pulling the probe, thereby testing the tensile strength of the electrode with respect to the substrate, comprising substrate support means for supporting the substrate, and probe guiding means for guiding the probe to the electrode on the substrate supported by the substrate support means.

In a preferred embodiment, the probe guide means has a plate-like member having a probe inserting hole, the substrate support means has a support for supporting the plate-like member to be substantially parallel to the substrate, and the support serves to support the plate-like member such that, when the probe is inserted in the hole in the plate-like member and the distal end portion thereof abuts against the electrode on the substrate supported by the substrate support means, at least part of the rod-like portion of the probe projects to that side of the plate-like portion which opposes the substrate.

Further, according to the present invention, the foregoing object is also attained by providing an electrode-probe bonding device for an electrode tensile test, comprising heating means having a heater and capable of soldering an electronic component, substrate support means for supporting the substrate, and probe guiding means for guiding the probe to the electrode on the substrate supported by the substrate support means.

In a preferred embodiment, the guiding means guides a plurality of probes to a plurality of electrodes on the substrate.

In a preferred embodiment, the heating means comprises a chamber in which the substrate and the probe are placed, and means for blowing heated air into the chamber, thereby heating an interior of the chamber.

In a preferred embodiment, the heating means further comprises means for blowing at least nitrogen into the chamber.

In a preferred embodiment, the heating means comprises substrate heating means for heating the substrate in order to transmit heat to the electrode through the substrate.

In a preferred embodiment, the substrate support means supports the substrate to face down, the probe guiding means supports the probe to face up, and the substrate support means and the probe guiding means are arranged such that the substrate is located above the probe.

In a preferred embodiment, the substrate support means has positioning means for defining the distance between a distal end of the probe and the substrate.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 10A to 10O are views showing different types of probes used in the electrode tensile test according to the first embodiment of the present invention;

FIG. 14 is a sectional view for explaining the electrode fusing process and the probe inserting process in the electrode tensile test according to the third embodiment of the present invention.

DETAILED DESCRIPTION OF THE PREFERRED EMBODIMENTS

The preferred embodiments of the present invention will be exemplified in detail with reference to the accompanying drawings. The relative positions of components, the numerical formulae, the numerical values, and the like described herein are not intended to limit the scope of the claims of the invention unless specifically noted. To apply heat to an electrode "directly" refers to apply heat to the electrode via a route other than a probe.

[First Embodiment]

The first embodiment exemplifies an electrode tensile test method and apparatus which use a semiconductor chip as an example of a substrate to be tested and examine the bonding strength of a bump electrode on the chip.

Figure 1:
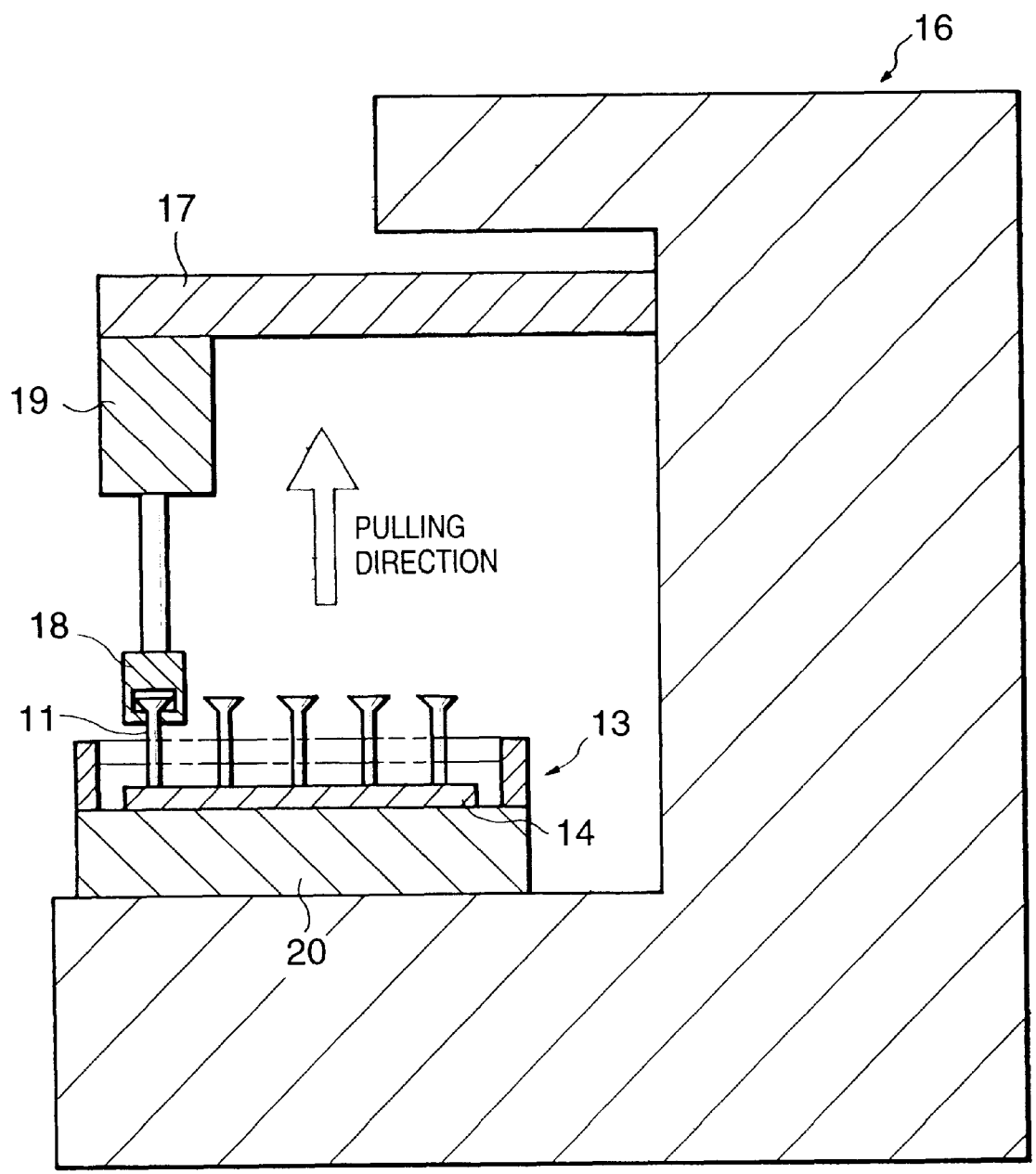
FIG. 1 is a view of the schematic arrangement of an electrode tensile test apparatus according to the first embodiment of the present invention.

FIG. 1 shows the overall arrangement of a test apparatus according to the first embodiment of the present invention.

An apparatus main body 16 formed as a C shape, and has a worktable 20 on which a semiconductor chip 14 is placed, a pulling tool 18 to various positions for pulling a probe 11 fixed to the semiconductor chip 14, a load cell 19 for measuring the force applied to the pulling tool 18, and a movable portion 17 for moving the pulling tool 18 in accordance with the probe 11.

The semiconductor chip 14 and probes 11 are supported by a support 13, and are fixed to the worktable 20 together with the support 13.

Figure 2:
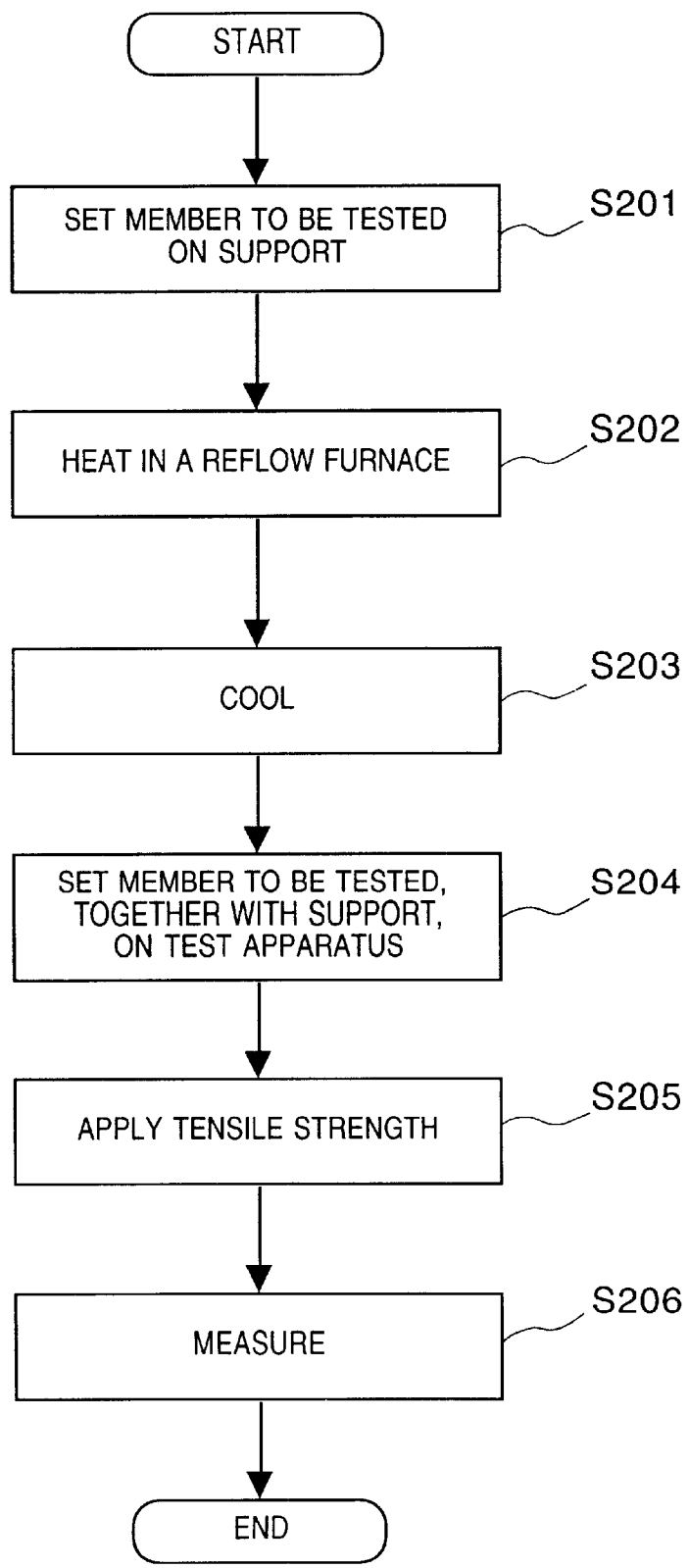
FIG. 2 is a flow chart of the test procedure using the electrode tensile test apparatus according to the first embodiment of the present invention.

FIG. 2 is a flow chart for explaining the procedure of conducting a test by using this test apparatus.

First, in step S201 the semiconductor chip 14 as the member to be tested, and the probes 11 are set on the support 13.

FIGS. 3 to 6 are views for explaining how to set the probes 11 and semiconductor chip 14 on the support 13.

Figure 3:
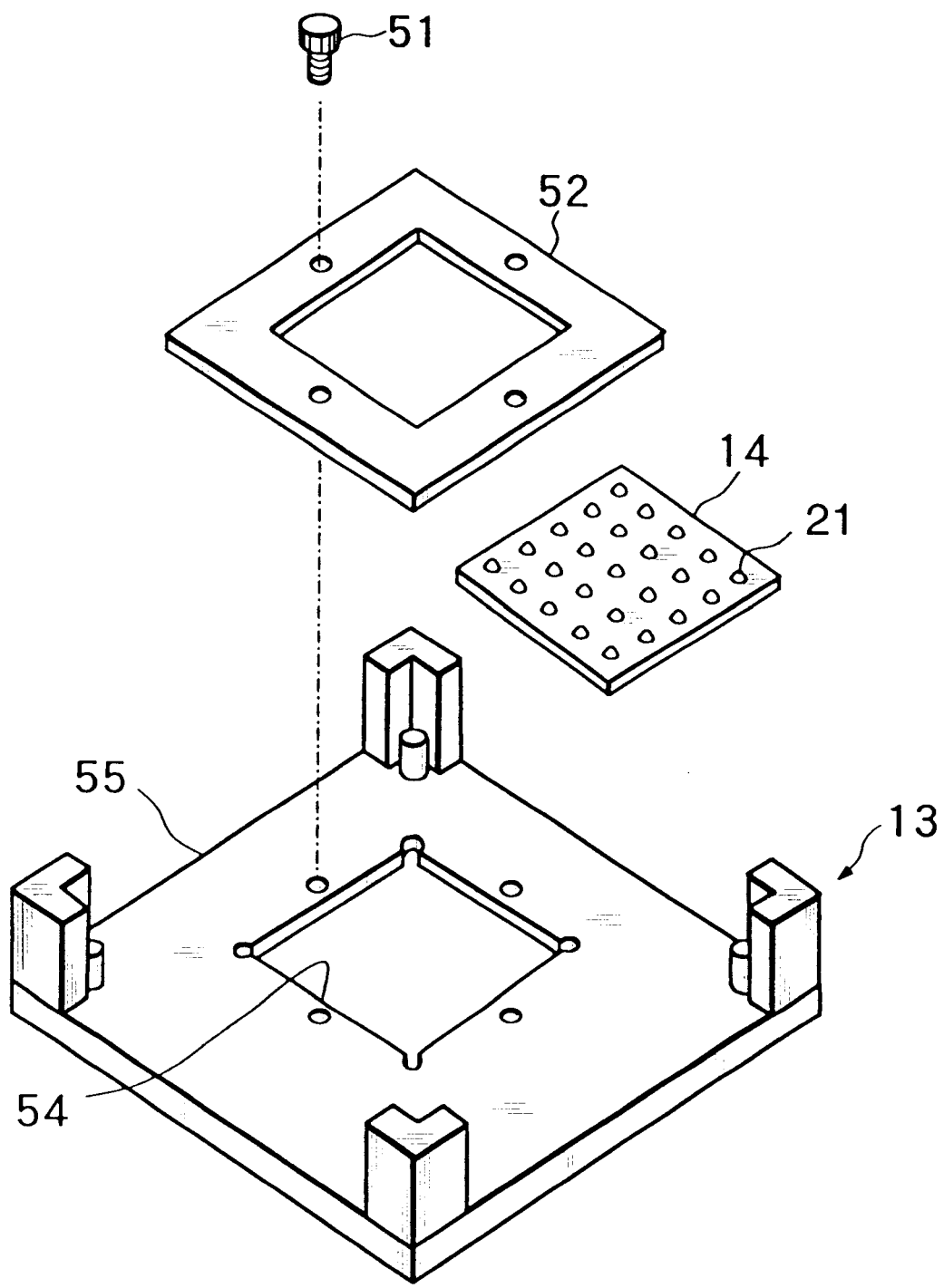
FIG. 3 is a view for explaining how to set a member to be tested on a support in the electrode tensile test according to the first embodiment of the present invention.

Referring to FIG. 3, a base plate 55 has such a structure at its lower portion where the electronic component or semiconductor component can be fixed. Also, the sample can be aligned with the base plate 55 easily. The semiconductor chip 14 is placed in a sample pocket 54, and a sample fixing plate 52 is fixed with set screws 51.

Figure 4:
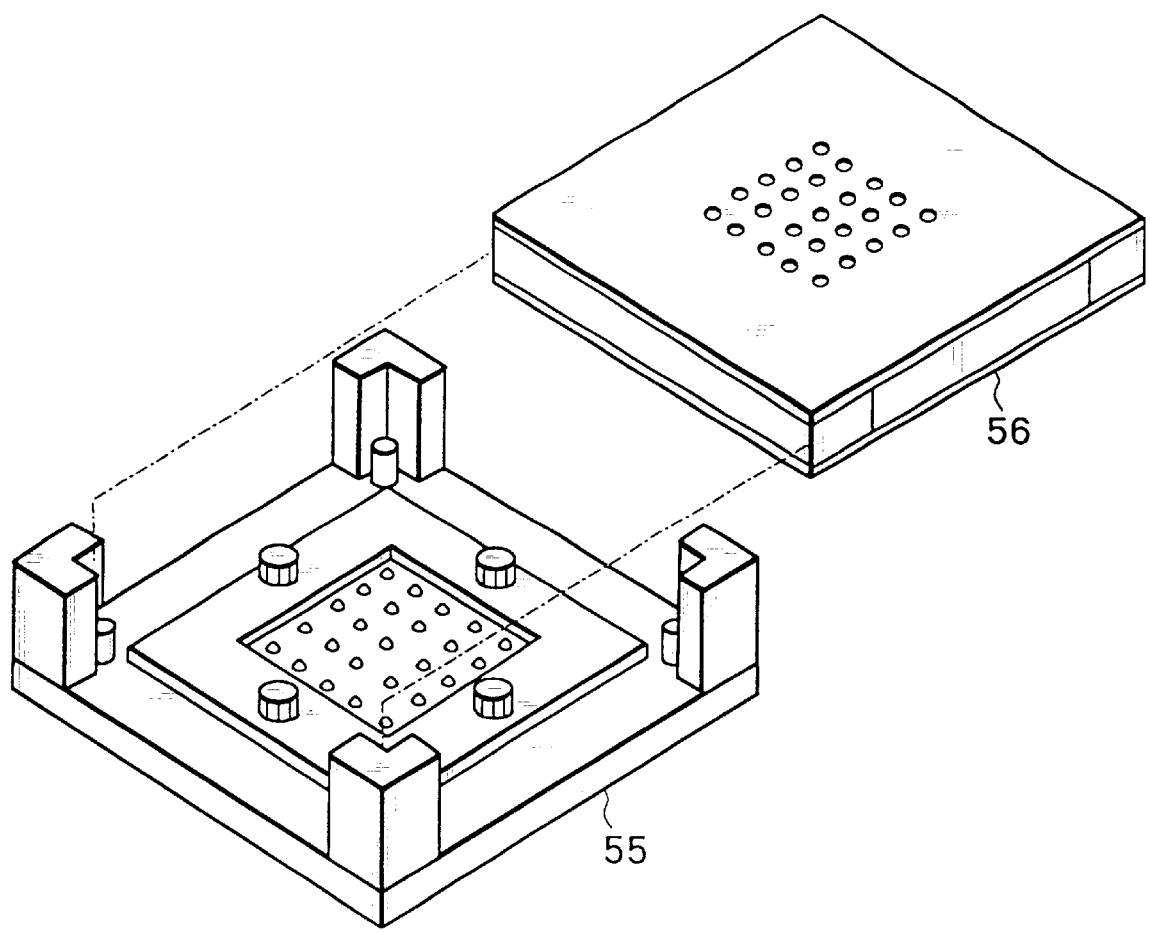
FIG. 4 is a view for explaining how to fix the base plate and the probe plate in the electrode tensile test according to the first embodiment of the present invention.
Figure 5:
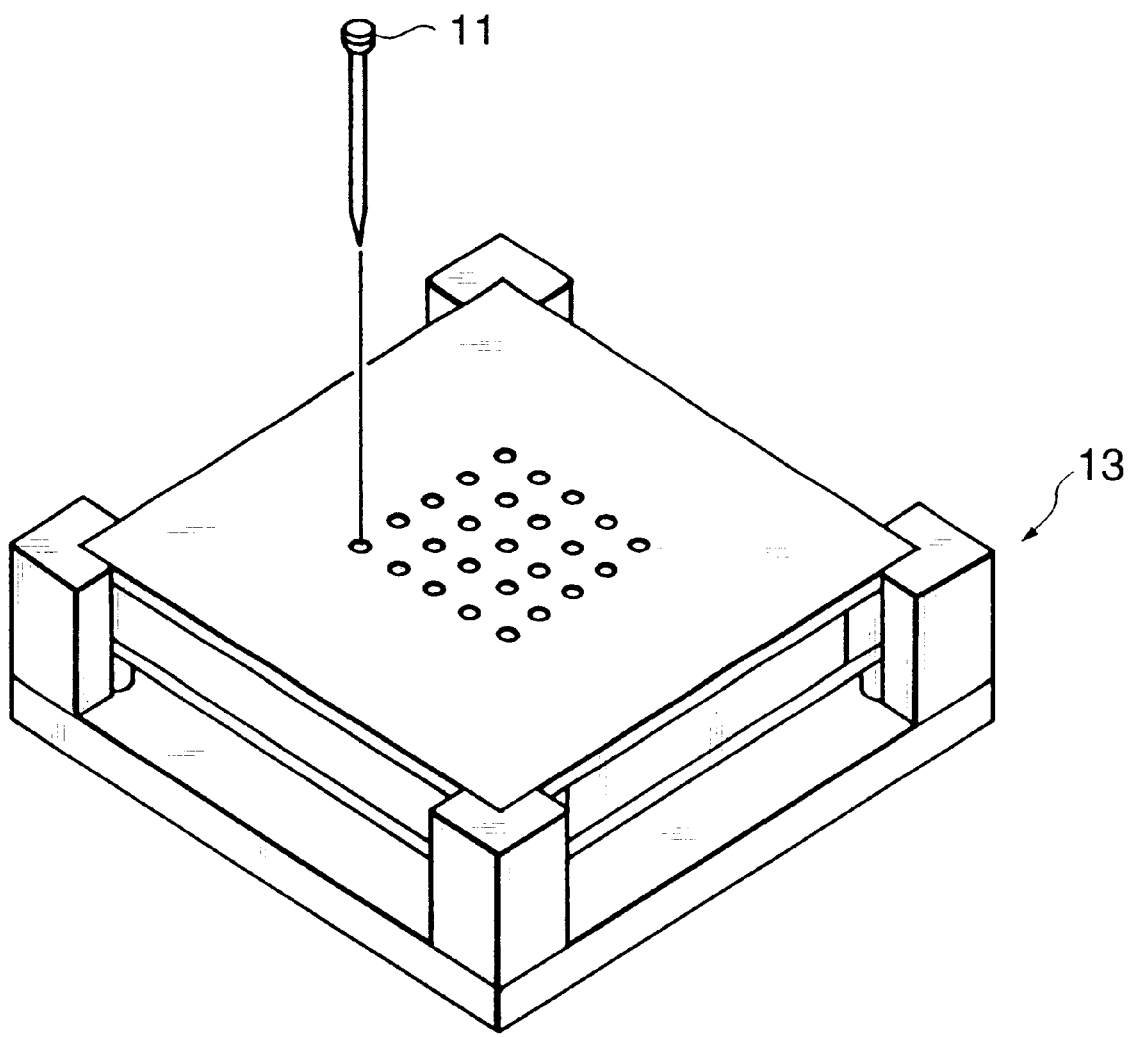
FIG. 5 is a view for explaining how a probe is inserted in the holes of the probe plate in the electrode tensile test according to the first embodiment of the present invention.

As shown in FIG. 4, a probe plate 56 is fitted with columns formed on the base plate 55. As shown in FIG. 5, an arbitrary number of probes 11 are inserted in holes in the probe plate 56.

Figure 6:
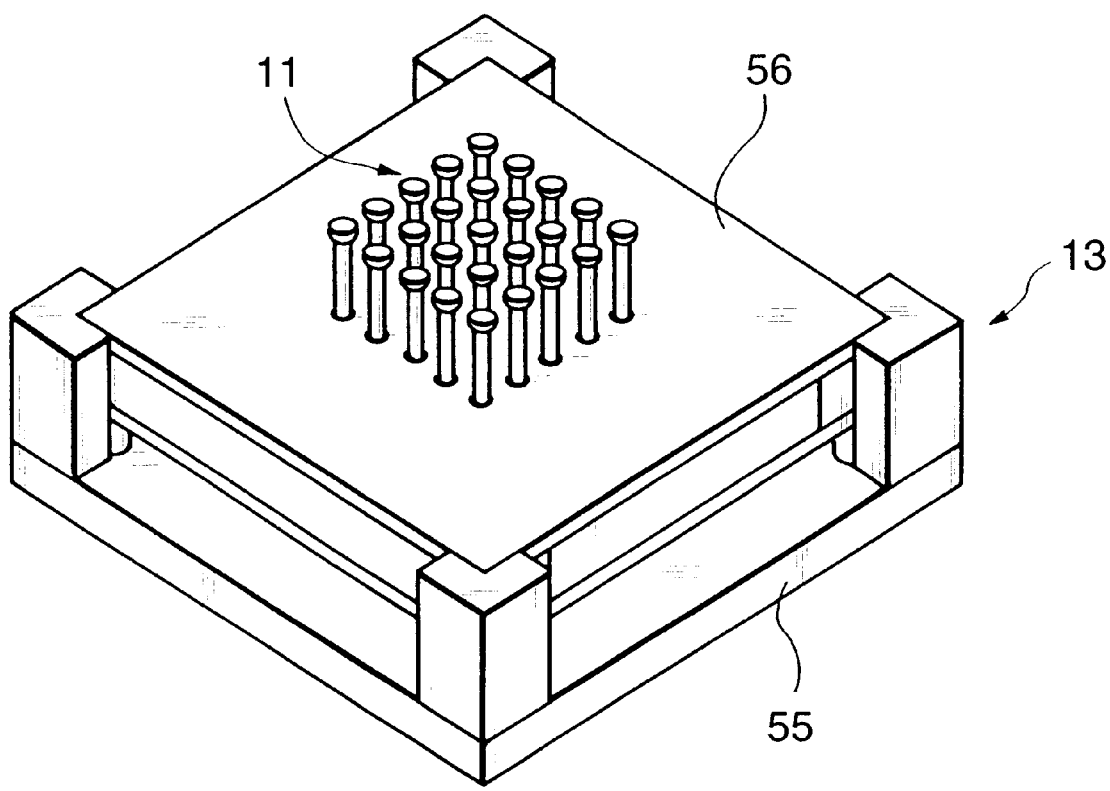
FIG. 6 is a view shows the assembled base plate and probe plate in the electrode tensile test according to the first embodiment of the present invention.
Figure 7:
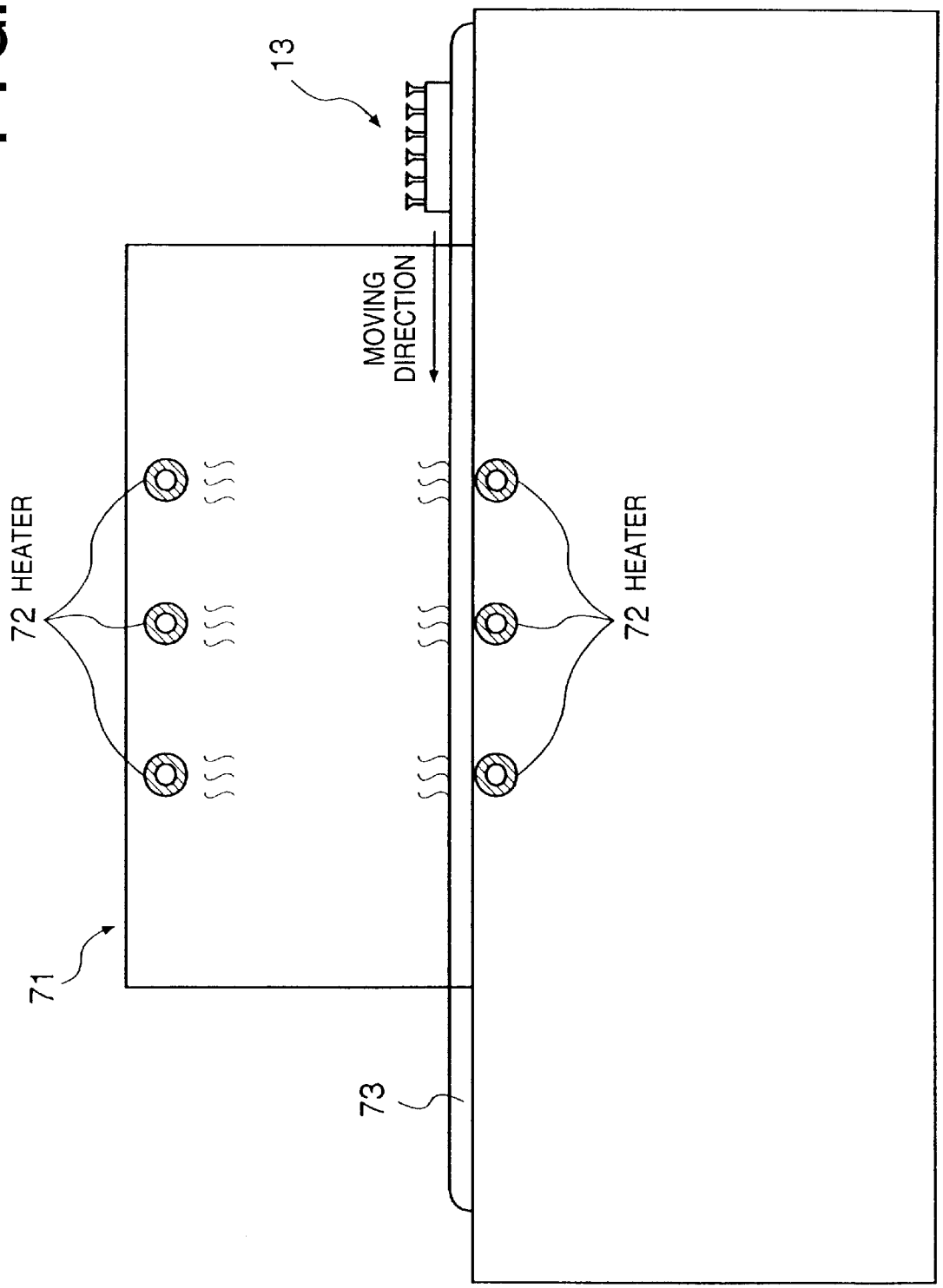
FIG. 7 is a view for explaining how to insert the member to be tested in a reflow furnace in the electrode tensile test according to the first embodiment of the present invention.

This leads to a state as shown in FIG. 6. In this state, the flow advances to step S202 of FIG. 2. More specifically, the semiconductor chip 14, probes 11, and support 13 set as shown in FIG. 6 are placed in a reflow furnace (any device which has a heater or the like and can solder and bond an electronic component or the like will do) actually used in a packaging process. The ambient temperature is increased to apply heat to the bump electrodes directly, thus fusing them. FIG. 7 shows this state.

Reference numeral 71 denotes a reflow furnace. The reflow furnace 71 has a plurality of heaters 72 in its upper and lower portions. A belt conveyor 73 is set on the bottom surface of the reflow furnace 71 to move the support 13, on which the probes 11 and semiconductor chip 14 are set, as shown in FIG. 7. During movement, the probes 11 and the semiconductor chip 14 are heated by the heaters 72, so the bump electrodes on the chip 14 fuse. As the reflow furnace, one used in manufacture of ordinary semiconductor chips can be used. As a result, a test result closer to the tensile strength between a bump electrode and a substrate that are connected in the actual manufacturing process can be obtained.

Figure 8:
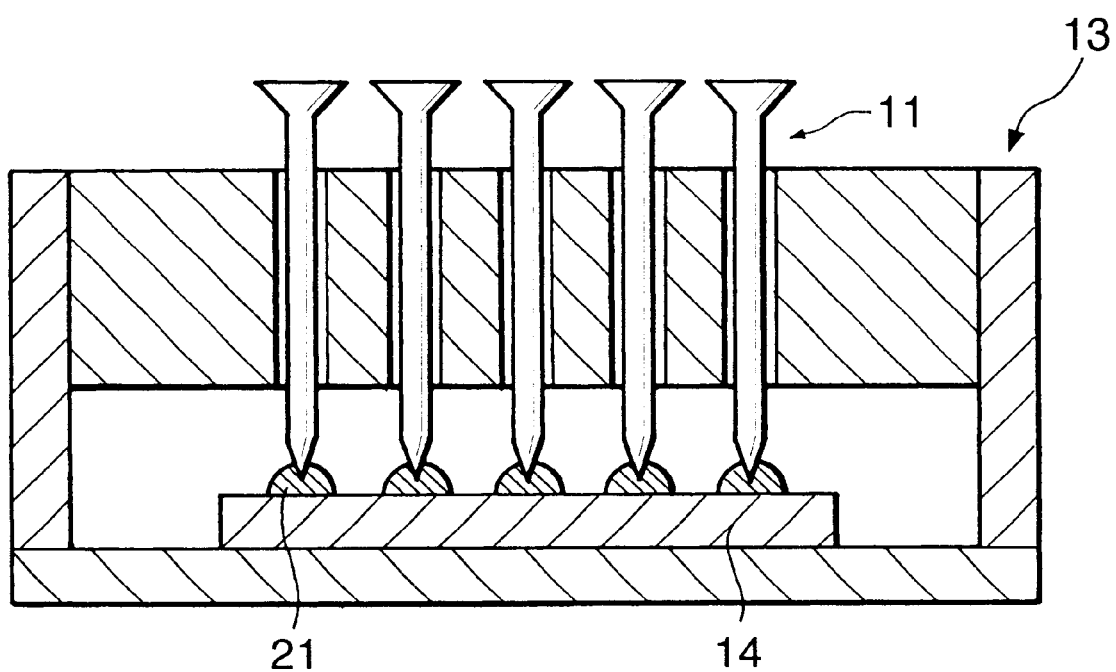
FIG. 8 is a view for explaining how probes are inserted in fused bump electrodes in the electrode tensile test according to the first embodiment of the present invention.

FIG. 8 is a sectional view of the support 13 on which the semiconductor chip 14 and probes 11 are set. When bump electrodes 21 fuse in the above manner, the probes 11 are inserted into the bump electrodes 21 by their own weights.

When the state as shown in FIG. 8 is reached, the support 13 with the semiconductor chip 14 and probes 11 is extracted from the reflow furnace. The flow advances to step S203 of FIG. 2, and waits until the support 13 is cooled to near room temperature. This fixes the bump electrodes 21 and probes 11 to each other.

Figure 9:
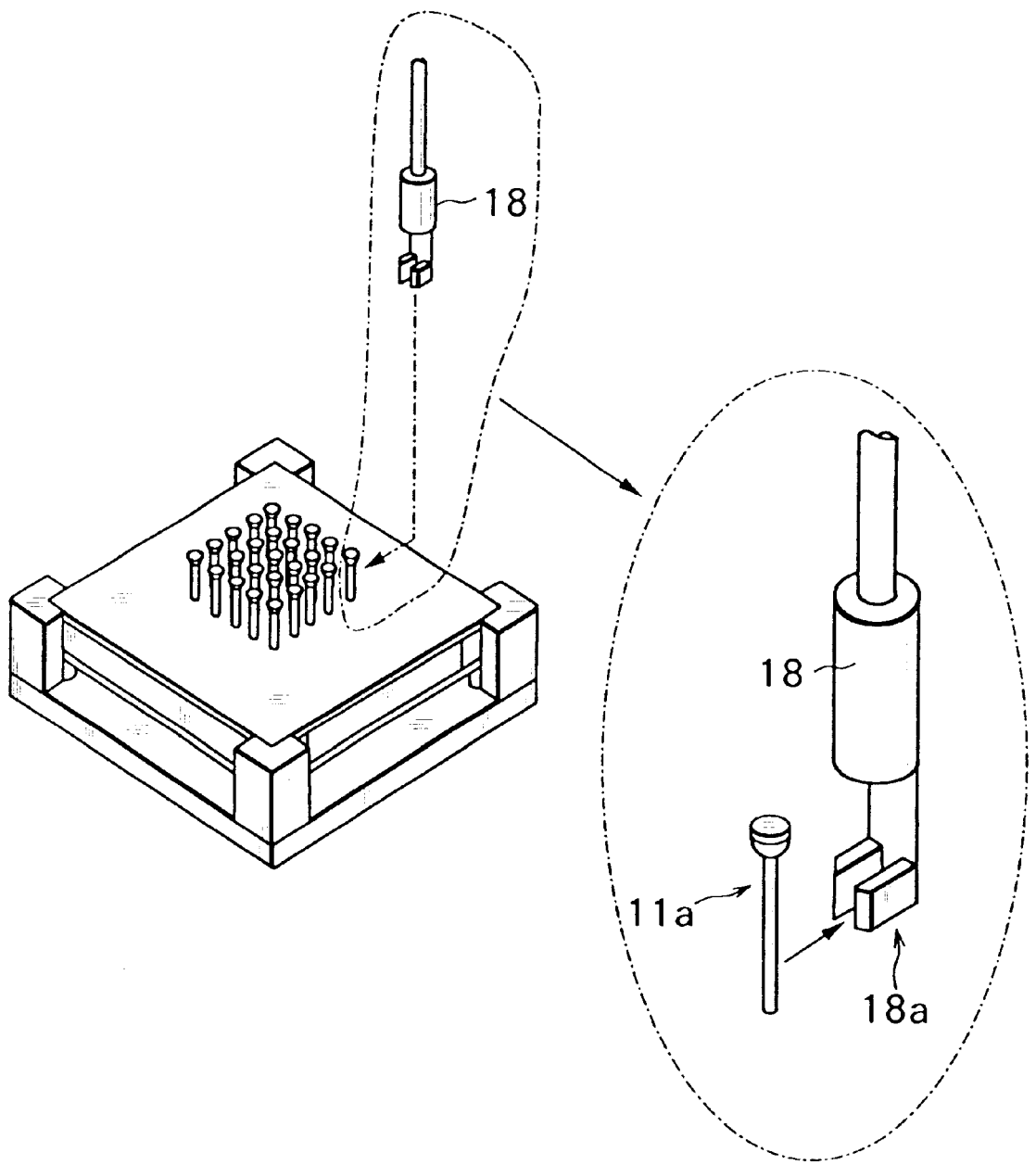
FIG. 9 is a view for explaining how to connect a pulling tool to the probe in the electrode tensile test according to the first embodiment of the present invention.

The flow advances to step S204 of FIG. 2. The semiconductor chip 14 and probes 11 are fixed to the worktable 20 of the test apparatus main body 16 together with the support 13. The flow advances to step S205 of FIG. 2. As shown in FIG. 9, the probes 11 are pulled in the vertical direction by using the pulling tool 18 until the bump electrodes 21 separate from the semiconductor component 14.

In this case, an upper end portion 11a of each probe 11 is formed to have a large diameter. The upper end portion 11a is hung on the edge of a slit 18a of the pulling tool 18, and the pulling tool 18 is pulled upward.

The flow advances to step S206 of FIG. 2. The tensile strength between the bump electrodes 21 and the substrate bonded to each other is measured by the load cell 19. This is performed by measuring the change in tensile force between the start of pulling and the separation of the bump electrodes. In particularly, the tensile strength is the moment when the bump electrodes separate from the substrate.

In this embodiment, the reflow furnace as the electrode fusing means can apply a temperature condition almost the same as that in the packaging process. Therefore, the tensile strength between the bump electrodes and the substrate land can be accurately tested in units of bump electrodes.

After the plurality of probes are connected to the bump electrodes in advance, the probes are pulled individually to test the tensile strength between the bump electrodes and the substrate bonded to each other. Therefore, the test can be done efficiently.

In this embodiment, the probes are inserted after the bump electrodes on the semiconductor chip have fused. However, the present invention is not limited to this, and the bump electrodes can be fused while the probes are inserted in them.

The probes may be needle-like members made of a metal such as copper, a copper-containing alloy, or nickel, or a ceramic material. Desirably, the probes are made of such a material that they do not stretch easily by the pulling force. The probes also must have a certain degree of a heat resistance.

The shape of the probes can be various; for example, its distal end portion can be as shown in FIGS. 10A to 10C, or FIG. 10N or 10O, its distal end portion can have a section as shown in FIG. 10D or 10E, its upper end portion can be as shown in FIGS. 10F to 10L, or it can be cylindrical, as shown in FIG. 10M. In particular, if the distal end portion of the probe has a section as shown in FIG. 10D or 10E, it provides a large contact area with the bump electrode. Then, the bump electrode and the probe will not separate from each other easily, so that the tensile strength between the substrate and the bump electrode can be tested more reliably. If the distal end portion of the probe is formed as shown in FIG. 10N or 10O, misalignment between the electrode and the probe in the horizontal direction is reduced, and the probe will not detach from the electrode, so an accurate tensile test can be done.

The pulling tool may be formed to match the shape of the upper end portion of the probe, and can be, e.g., one which clamps the upper end portion of the probe, or one from which the probe hangs.

Alternatively, the distal end portion of the probe may be coated with solder (or the land may be printed with a creamed solder). The land and the probe may be fused and bonded to each other, and the probe may be pulled in the vertical direction. The tensile strength of the land itself may be tested in this manner.

[Second Embodiment]

An electrode tensile test method and apparatus according to the second embodiment of the present invention will be described with reference to FIG. 11.

In the first embodiment, a reflow furnace is used to fuse the electrodes. In the second embodiment, a chamber 74 is used to fuse the electrodes. Except for this, the structures and processing steps are identical to those of the first embodiment. Accordingly, the same structures are denoted by the same reference numerals as in the first embodiment, and a detailed description thereof will be omitted.

Figure 11:
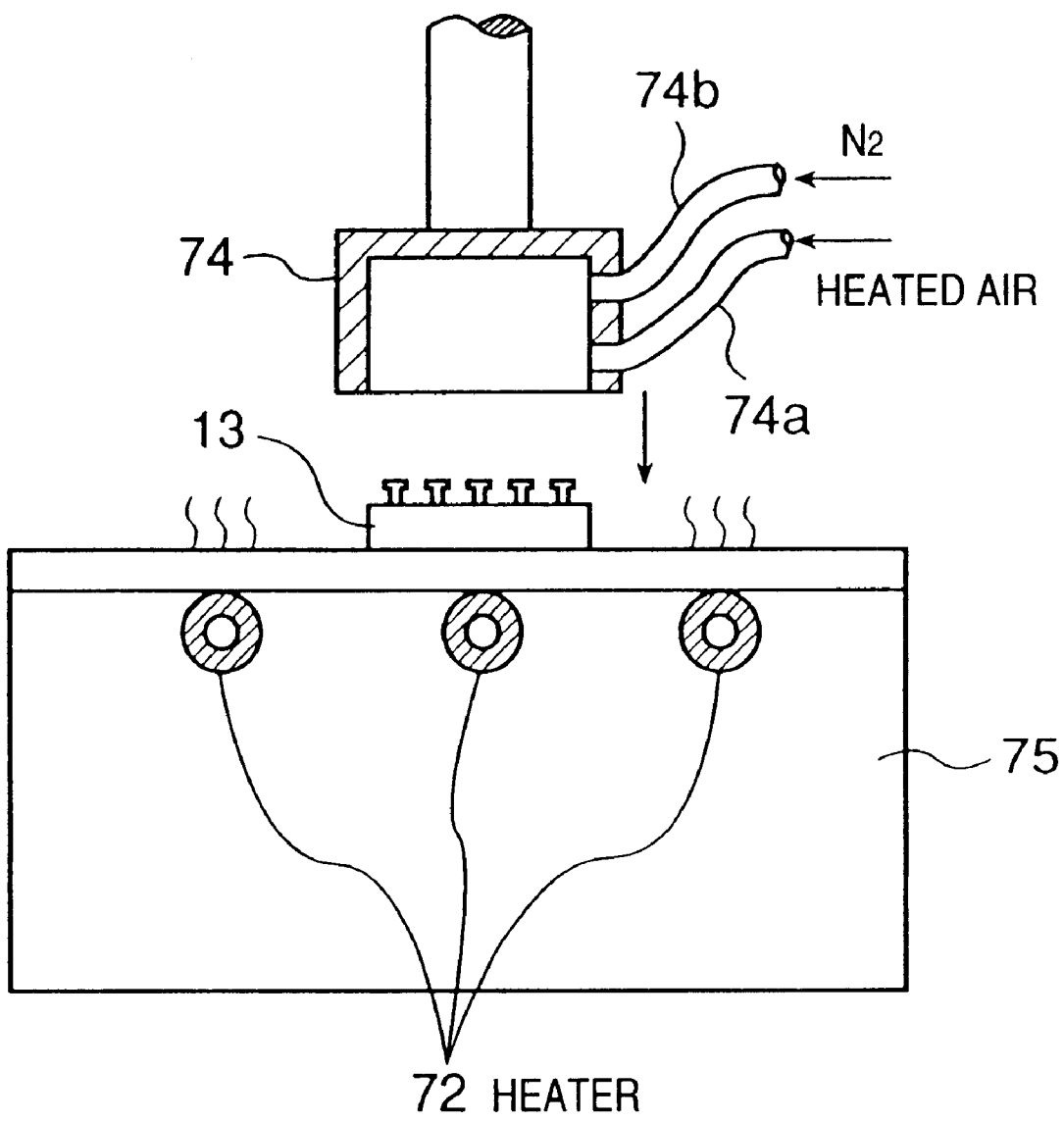
FIG. 11 is a view for explaining an electrode fusing process in an electrode tensile test according to the second embodiment of the present invention.

Referring to FIG. 11, the chamber 74 has a space that can house the probes and a semiconductor chip entirely, and has ports 74a and 74b to provide heated air and nitrogen into this space.

A base 75 where a support 13 is to be placed is provided with heaters 72.

First, the support 13 on which probes and a semiconductor chip are set is placed at a predetermined position on the base 75. The heaters 72 are used to pre-heat. Heat is transmitted from the lands of the semiconductor chip to the electrodes, to increase the temperature of the electrodes. After pre-heating for a predetermined period of time, the heaters 72 are turned off. The chamber 74 is moved downward to surround the support 13 entirely. In this state, heated air and nitrogen are blown through the ports 74a and 74b to increase the ambient temperature in the chamber 74, thereby fusing the electrodes. When nitrogen is provided, the oxygen concentration in the chamber 74 decreases. This prevents oxidation of the surfaces of the electrodes and improves adhesion between the bump electrodes and the probes.

The ambient temperature in the chamber 74 is sufficiently increased to fuse the electrodes, and then the probes are inserted in the electrodes by their self weights. In this state, the chamber 74 is moved upward to cool the support 13.

Processes after this are identical to those of steps S203 to S206 of FIG. 2 described in the first embodiment.

In the second embodiment, heated air and nitrogen are supplied into the chamber 74. Alternatively, high-temperature nitrogen may be supplied instead. Then, the oxygen concentration in the chamber 74 further decreases, so that the adhesion between the probes and electrodes improves and the probes can be inserted in the electrodes more easily.

As the cooling process, cool air may be supplied into the chamber 74. In this case, the electrodes and probes can be cooled more efficiently.

Pre-heating is performed by using the heaters 72 provided to the base 75, because when the electrode temperature is increased to a certain degree prior to main heating by the chamber 74, the adhesion between the probes and electrodes improves. Generally, pre-heating is also performed in packaging process. Therefore, the tensile test can be run with electrodes set in a state closer to the actual packaged state.

The outputs from the heaters 72 provided to the base 75 may be increased so the heaters 72 can be used as the main heaters. In this case, the chamber 74 becomes unnecessary.

[Third Embodiment]

An electrode tensile test method and apparatus according to the third embodiment of the present invention will be described with reference to FIGS. 12 and 13.

In the first embodiment, the probes are inserted downward into a semiconductor chip facing up. In the third embodiment, a BGA (Ball Grid Array) package as an example of a substrate is placed to face down with respect to probes facing up, and the probes are inserted into the electrodes by the self weight of the package. Except for this, the arrangements and processing steps are identical to those of the first embodiment. Accordingly, the same arrangements are denoted by the same reference numerals as in the first embodiment, and a detailed description thereof will be omitted.

Figure 12:
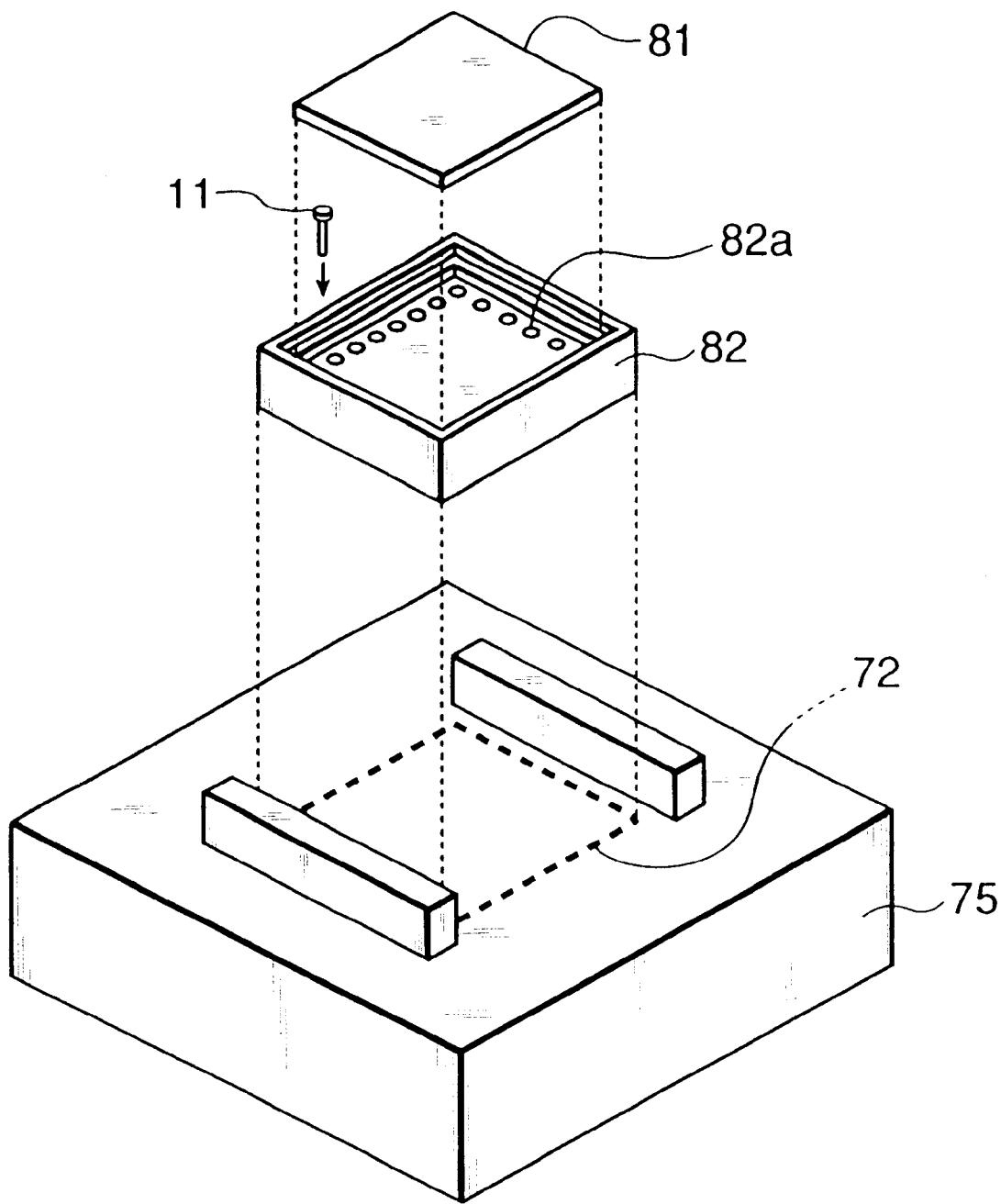
FIG. 12 is a view for explaining the arrangement of a package and a probe in an electrode tensile test according to the third embodiment of the present invention.

FIG. 12 shows the process of attaching probes 11 and a package 81 to a support 82 and placing the resultant structure on a base 75.

The support 82 forms a square shape, and has a base plate and walls. The base plate has a plurality of probe guiding holes 82a to serve as a probe guide means. The inner diameter of each hole 82a is slightly larger than the probe diameter. Hence, the probe does not tilt greatly when it is inserted in the hole 82a, and can be inserted and removed into and from the hole 82a smoothly. The positions of the holes 82a correspond to the positions of the respective electrodes on the package 81.

First, the support 82 is placed on the base 75, and the probes 11 are inserted in the respective holes 82a. In this state, the package 81 is fitted in the cylindrical portion of the support 82. The base 75 incorporates a pre-heating heater 72 to apply heat to the support 82. In this case, a heater 72 having a shape matching the support 82, as shown in FIG. 12, is built in the base 75.

Figure 13:
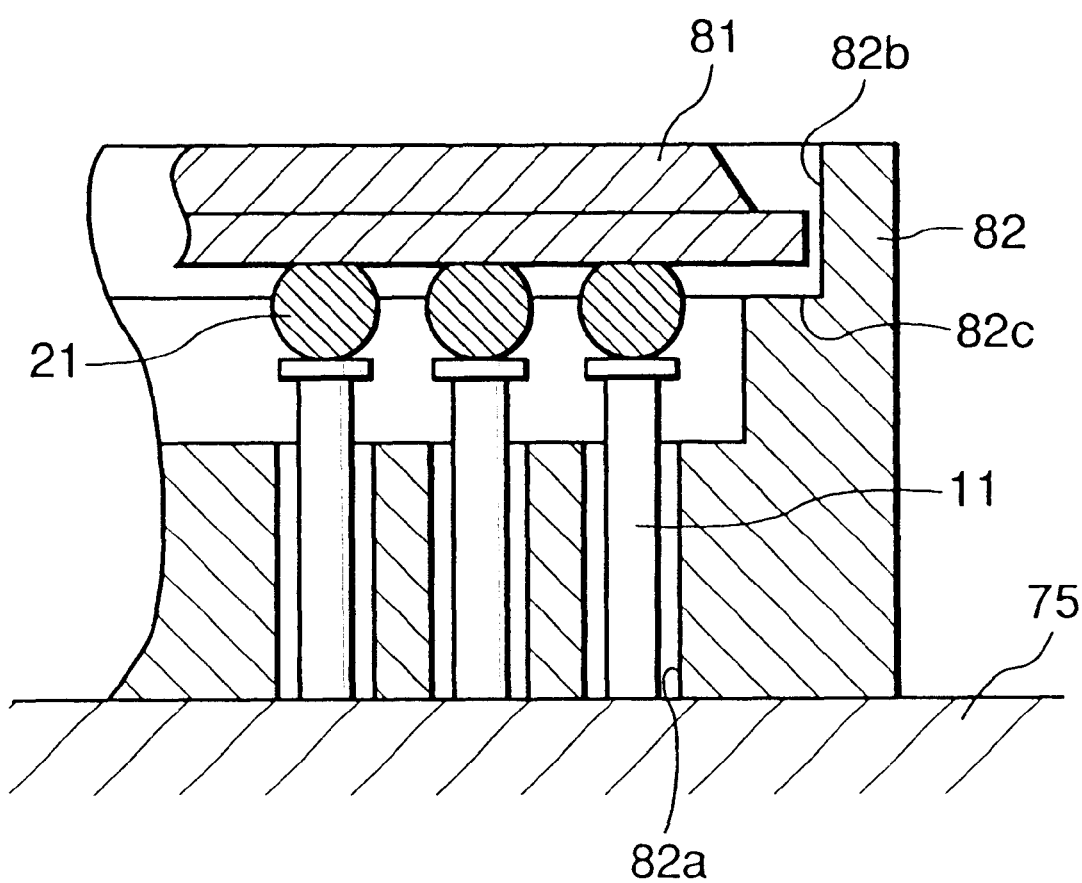
FIG. 13 is a sectional view for explaining an electrode fusing process and a probe inserting process in the electrode tensile test according to the third embodiment of the present invention.

FIG. 13 is a sectional view showing a state wherein the support 82 on which the probes 11 and package 81 are set is placed on the base 75.

As shown in FIG. 13, the thickness of the bottom portion of the support 82 is smaller than the length of each probe 11. While the probes 11 are inserted in the holes 82a, the distal ends of the probes 11 are present outside the holes 82a.

Before electrodes 21 are fused, they abut against the probes 11, thereby supporting the package 81. At this time, a side wall 82b of the support 82 serves as the positioning means for the package 81, so that the probes 11 come into contact with the respective electrodes 21 precisely.

FIG. 14 shows a sectional view showing the state wherein the electrodes 21 have fused and the probes 11 are inserted in them.

As shown in FIG. 14, when the bump electrodes 21 fuse, the package 81 moves downward on its self weight, and the probes 11 are inserted in the bump electrodes 21. Since the support 82 is formed with a package positioning portion 82c, movement of the package 81 stops when the distal ends of the probes 11 are inserted into the electrodes 21 for a predetermined length. The probes 11 will not extend through the electrodes 21 to abut against the package main body, and all the probes 11 are inserted into all the corresponding electrodes 21 for the predetermined length. Therefore, the precision of the electrode tensile test improves greatly.

The electrodes 21 may be fused in a reflow furnace, as in the first embodiment, or in a chamber, as in the second embodiment. Alternatively, the electrodes 21 may be fused by only the heaters 72 provided to the base 75.

Once the state shown in FIG. 14 is reached, the electrodes 21 and probes 11 are cooled, and are subjected to the tensile test. These processes are identical to those described in the first or second embodiment, and a detailed description thereof will accordingly be omitted.

When the electrodes are arranged above the probes as described above, the fused probes impart better adhesion with the probes below them because of their self weight, and the probes can be inserted into the electrodes for the predetermined length easily.

In the third embodiment, the probes are inserted into the fused electrodes by the self weight of the probes or package. However, the present invention is not limited to this. The probes may be inserted into the electrodes by applying a force to the probes or package.

In the third embodiment, probe guiding holes are formed in the support to correspond to the positions of the electrodes on the substrate or package. However, the present invention is not limited to this. Many probe guiding holes may be formed, and the probes may be inserted into only holes corresponding to the positions of the electrodes.

Sometimes the electrodes may be fused by increasing the ambient temperature by using a reflow furnace or a chamber. In this case, if a slit is formed in the side wall of the support 13 or 82 so that high-temperature air can flow toward the electrodes, then the electrodes can be fused within a shorter period of time.

According to the embodiments described above, a plurality of electrodes can be bonded to a plurality of probes simultaneously in a state closer to that in an actual packaging process. Therefore, the electrode tensile strength can be obtained accurately and efficiently.

As many apparently widely different embodiments of the present invention can be made without departing from the spirit and scope thereof, it is to be understood that the invention is not limited to the specific embodiments thereof except as defined in the appended claims.

What is claimed is:

1. An electrode tensile test method of fixing a probe to an electrode on a substrate, and pulling said probe, thereby testing a tensile strength of the electrode with respect to the substrate, comprising:

a substrate setting step of setting the substrate having said electrode on a support member;

a plate setting step of setting a plate having a probe insertion hole on the above and substantially parallel to said substrate on said support member substantially parallel to the substrate;

a probe inserting step of inserting said probe into the probe insertion hole in order to make an end of said probe contact to the electrode on the substrate;

an electrode fusing step of fusing the electrode so that the end of said probe enters the fused electrode by self weight of said probe;

a cooling step of cooling the electrode together with said probe; and a measuring step of pulling said probe, which has been fixed to the electrode through the cooling step, from the substrate, and measuring the tensile force between the electrode and the substrate.

2. The method according to claim 1, wherein the electrode fusing step is a step to increase ambient temperature in a space about said probe and the electrode.

3. The method according to claim 1, wherein in the electrode fusing step a unit comprising of the substrate, the plate and said probe inserted into the hole in the plate is heated in a reflow furnace.

4. The method according to claim 1, wherein the electrode fusing step is a step to place a unit comprising of the substrate, the plate and said probe inserted into the hole in the plate in a chamber, and blowing heated air into said chamber, thereby heating the interior of said chamber.

5. The method according to claim 4, wherein the electrode fusing step comprises blowing at least nitrogen into said chamber.

6. The method according to claim 1, wherein the electrode fusing step comprises the step of applying heat to the electrode through the substrate.

7. The method according to claim 1, wherein in said inserting step, a plurality of probes are inserted into a plurality of holes in the plate, respectively, and in each of the electrode fusing step, and the cooling step, a plurality of electrodes on one substrate and a plurality of probes corresponding thereto are processed simultaneously.

8. An electrode tensile test apparatus for fixing a probe to an electrode and pulling said probe, thereby testing the tensile strength of the electrode with respect to a substrate, comprising:

substrate support means for supporting the substrate;

probe guiding means for guiding said probe to the electrode on the substrate supported by said substrate support means; and measuring means for catching and pulling one end of said probe, which is fixed to the electrode on the substrate, and measuring a tensile force between the electrode and the substrate, wherein said probe guiding means has a plate member having a probe insertion hole, and said substrate support means has a support for supporting said plate member to be substantially parallel to the substrate, said support serving to support said plate member such that said probe is inserted in the hole in said plate member and a distal end portion thereof abuts against the electrode on the substrate supported by said substrate support means.

9. The apparatus according to claim 8, further comprising heating means for increasing ambient temperature of space containing said probe and the electrode.

10. The apparatus according to claim 9, wherein said heating means is a reflow furnace.

11. The apparatus according to claim 9, wherein said heating means comprises:
   a chamber in which the substrate and said probe are placed; and
   means for blowing heated air into said chamber, thereby heating an interior of said chamber.

12. The apparatus according to claim 11, wherein said heating means further has means for blowing at least nitrogen into said chamber.

13. The apparatus according to claim 8, further comprising substrate heating means for heating the substrate in order to transmit heat to the electrode through the substrate.

14. The apparatus according to claim 8, wherein the plate has a plurality of holes into which a plurality of probes are inserted respectively.

15. A substrate/probe support device for an electrode tensile test for fixing a probe and an electrode on a substrate to each other by using heating means which increases an ambient temperature, and pulling said probe, thereby testing the tensile strength of the electrode with respect to the substrate, comprising:
   substrate support means for supporting the substrate; and
   probe guiding means for guiding said probe to the electrode on the substrate supported by said substrate support means;
   wherein said probe guide means has a plate member having a probe inserting hole, and said substrate support means has a support for supporting said plate-like member to be substantially parallel to the substrate, said support serving to support said plate-like member such that said probe is inserted into the hole in said plate member and the distal end portion thereof abuts against the electrode on the substrate supported by said substrate support means.

16. The device according to claim 15, wherein at least part of a rod-like portion of said probe projects to that side of said plate-like portion which opposes the substrate.

17. An electrode tensile test apparatus for fixing a probe to an electrode and pulling said probe, thereby testing the tensile strength of the electrode with respect to a substrate, comprising:
   probe support means for supporting said probe upwardly, said probe support means includes a plate having at least one hole for inserting said probe;
   substrate guiding means for downwardly guiding the substrate to said probe such that the electrode on the substrate comes into contact with the distal end of said probe which is inserted into the hole in the plate; and
   measuring means for catching and pulling said probe, which is fixed to the electrode on the substrate, and measuring a tensile force between the electrode and the substrate.

* * * * *